US006462022B1

United States Patent
Roberts et al.

(10) Patent No.: US 6,462,022 B1
(45) Date of Patent: Oct. 8, 2002

(54) LISINOPRIL COMPOSITIONS HAVING LARGE-PARTICLE DCPD

(75) Inventors: Ronald John Roberts; David Brandon Bowen, both of Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/962,429

(22) Filed: Sep. 24, 2001

(51) Int. Cl.$^7$ .............................................. C07K 5/087
(52) U.S. Cl. ........................ 514/18; 514/19; 530/331; 424/464; 424/465; 424/469; 424/489; 424/602; 423/304; 423/305; 426/267
(58) Field of Search .................... 514/19, 18; 424/464, 424/469, 489, 465, 602; 423/304, 305; 426/267; 530/331

(56) References Cited

U.S. PATENT DOCUMENTS

| | | | | |
|---|---|---|---|---|
| 4,517,179 A | * | 5/1985 | Raghunathan | 514/24 |
| 4,675,188 A | * | 6/1987 | Chu | 424/154 |
| 4,707,361 A | * | 11/1987 | Gustafson | 424/154 |
| 6,117,451 A | * | 9/2000 | Kumar | 424/465 |
| 6,210,715 B1 | * | 4/2001 | Starling | 424/489 |

OTHER PUBLICATIONS

Landin, M. Int. J. Pharm. 104(3), 271–5, 1994.*
Takami, Kiyoshi Chem. Pharm. Bull. 44(4), 868–70, 1996.*
Otsuka, Makoto J. Biomed. Mater. Res. 29(1), 25–32, 1995.*
Bavitz and Shiromani, 1986, "Granulation surface area as basis for magnesium stearate concentrations in tablet formulations", Drug Dev. Ind. Pharm. 12:2481–2492.
Ip et al., 1992, "Lisinopril", *Analytical Profiles Of Drug Substances And Excipients* vol. 21 (Academic Press) pp. 233–276.
Landin et al., 1994, "Chemical stability of acetylsalicylic acid tablets prepared with different commercial brands of dicalcium phosphate dihydrate", Int. J. Pharmaceutics 107:247.
Landin et al., 1994, "Dicalcium phosphate dihydrate for direct compression: characterization and intermanufacturer variability", Int. J. Pharmaceutics 109:1–8.
Landin, 1995, "Chemical stability of acetylsalicylic acid in tablets prepared with different particle size fractions of a commercial brand of dicalcium phosphate dihydrate", Int. J. Pharmaceutics 123:143–144.
Shiromani and Bavitz, 1988, "Studies on a dibasic calcium phosphate–mannitol matrix table formulation —a complementary combination", Drug Dev. Ind. Pharm. 14:1375–1387.
Wang et al., 2000, "Thermal–Dependent Dehydration Process and Intramolecular Cyclization of Lisinopril Dihydrate in the Solid State", Chem. Pharm. Bull. 48:1890–1893.

\* cited by examiner

*Primary Examiner*—Christopher S. F. Low
*Assistant Examiner*—David Lukton
(74) *Attorney, Agent, or Firm*—Ropes & Gray

(57) ABSTRACT

The present invention relates to a pharmaceutical composition comprising lisinopril and dibasic calcium phosphate dihydrate (DCPD), produced by a process comprising mixing lisinopril and DCPD with a specific surface area of less than 1.5 $m^2g^{-1}$. The use of large particle sized DCPD in a lisinopril formulation/composition has the effect of reducing the amount of the lisinopril degradation product DKP that is formed, thereby increasing the shelf-life of tablets formulated with the larger sized DCPD, particularly those with low doses of lisinopril.

12 Claims, No Drawings

LISINOPRIL COMPOSITIONS HAVING LARGE-PARTICLE DCPD

BACKGROUND OF THE INVENTION

The compound 1-($N^2$-[(S)-1-carboxy-3-phenylpropyl]-L-lysyl)-L-proline, having the generic name lisinopril, as well as therapeutically acceptable salts thereof, are described in U.S. Pat. Ser. No. 4,374,829 (Merck & Co. Inc.), incorporated herein by reference. In said patent the compound is described in Example 119, and is referred to as N-α-[1 (S)-1-carboxy-3-phenylpropyl]-L-lysyl-L-proline. The divisional application of the '829 patent, which has resulted in U.S. Pat. No. 4,472,380, incorporated herein by reference, claims pharmaceutical compositions that include lisinopril pharmaceutical compositions. Lisinopril is a drug on which extensive clinical experience has been obtained. It is currently sold in the United States under the trademark ZESTRIL® by AstraZeneca or PRINIVIL® by Merck & Co. A combination of lisinopril and hydrochlorothiazide is sold under the trademarks ZESTORETIC® by AstraZeneca or PRINZIDE® by Merck & Co. ZESTRIL® and ZESTORETIC® are manufactured by wet granulation tabletting using milled DCPD.

A typical lisinopril formulation consists of lisinopril dihydrate, which can be any dose from 1mg–100 mg, the fillers (diluents)-dibasic calcium phosphate dihydrate and mannitol, maize starch as a binder and disintegrant and magnesium stearate as a lubricant.

Lisinopril is a peptidyl dipeptidase inhibitor useful in treating cardiovascular diseases and disorders, such as hypertension and congestive heart failure (CHF) in mammals and especially in man. It inhibits the angiotensin converting enzyme (ACE) that catalyses the conversion of angiotensin I to the vasoconstrictor peptide, angiotensin II. Angiotensin II also stimulates aldosterone secretion by the adrenal cortex. Inhibition of ACE results in decreased concentrations of angiotensin II which results in decreased vasopressor activity and reduced aldosterone secretion.

ACE is known to be present in the endothelium and increased ACE activity in diabetic patients which results in the formation of angiotensin II and destruction of bradykinin, potentiates the damage to the endothelium caused by hyperglycaemia. ACE inhibitors, including lisinopril, inhibit the formation of angiotensin II and breakdown of bradykinin and hence ameliorate endothelial dysfunction.

Dibasic calcium phosphate dihydrate (DCPD, $CaHPO_4.2H_2O$) is a diluent used in tablet and capsule formulations. It is used both as an excipient (diluent/filler) and as a source of calcium in nutritional supplements. It is used in pharmaceutical products because of its compaction properties, and the good-flow properties, particularly the coarse-grade material. Two main particle-size grades of DCPD are used in the pharmaceutical industry, milled and unmilled. The former material is typically used in wet-granulated or roller-compacted formulations whereas the latter coarse-grade material is typically used in dry, direct-compression formulations.

Synonyms and trademarks for dibasic calcium phosphate dihydrate are: Cafos; calcium hydrogen orthophosphate dihydrate; calcium monohydrogen phosphate dihydrate; Calstar; Calipharm; dicalcium orthophosphate; Difos; DI-TAB; E341; Emcompress; phosphoric acid calcium salt (1:1) dihydrate; secondary calcium phosphate; calcium phosphate; and dicalcium phosphate, the latter two terms are commonly used generic terms in the pharmaceutical art.

Dibasic calcium phosphate dihydrate is white, odourless, tasteless, nonhygroscopic and stable at room temperature. However, under certain conditions of temperature and humidity, it can lose water of crystallization below 100° C.

On long-term storage, when in the formulated product and particularly with low dosage formulations, lisinopril has a tendency to form diketopiperazine (DKP), a lisinopril degradation product or metabolite, which limits the shelf life for low dose formulations. The inventors have found a correlation between the amount and speed of DKP formation and the particle size of the co-formulated dibasic calcium phosphate dihydrate excipient.

It has previously been disclosed that when formulated as a tablet with large particle sizes of DCPD, aspirin has a reduced propensity to degrade to salicylic acid and acetic acid compared to aspirin formulated as a tablet with smaller particle sized DCPD (Landin et al., (1994) Int. J. Pharm. 107:247–249; Landin et al., (1995) Int. J. Pharm. 123:143–144). The mechanism for the degradation of aspirin to salicylic acid and acetic acid is hydrolysis (Leesen and Mattocks (1958) J. Am. Pharm. Sci. Ed., 67:329–333.). DCPD, which is known to readily dehydrate, provides water to promote the process. The poorer stability of tablets containing powdered material of DCPD as compared to aggregated material was attributed to a greater propensity of smaller particle size DCPD to lose more water (Landin et al., 1994, 1995, supra).

The breakdown of lisinopril to form DKP is, however, not a hydrolysis (the addition of water) but dehydration (loss of water) within the lisinopril molecule. Because the mechanism of action involved with aspirin and lisinopril degradation are completely different, it would not have been predictable that use of larger particle sized DCPD would also reduce the amount of lisinopril degradation.

SUMMARY OF THE INVENTION

The present invention relates to a composition comprising 1-($N^2$-[(S)-1-carboxy-3-phenylpropyl]-L-lysyl)-L-proline and processes for making the composition. 1-($N^2$-[(S)-1-carboxy-3-phenylpropyl]-L-lysyl)-L-proline is known under the generic name lisinopril. The novel composition is made with dibasic calcium phosphate dihydrate (DCPD, $CaHPO_4.2H_2O$) that possesses a low specific surface area of less than 1.5 $m^2g^{-1}$ as determined by nitrogen adsorption (BET method). The use of large-particle DCPD in a lisinopril formulation/composition has the effect of reducing the amount of the lisinopril degradation product diketopiperazine (DKP) that is formed, which would increase the shelf-life of tablets formulated with the large-particle DCPD, particularly those containing low dosage amounts of lisinopril.

DETAILED DESCRIPTION OF THE INVENTION

It has surprisingly been found that the lisinopril tablets formulated with large particle sized DCPD (unmilled) have a reduced tendency to form the lisinopril degradation product, diketopiperazine (DKP), particularly in low dosage lisinopril tablets. It is an object of the present invention to provide lisinopril tablets that have been made with larger particle sized DCPD than currently used, with the intention of reducing the amount of DKP degradation product that forms.

The invention is not limited by the tabletting method. The large particle DCPD can be used to form lisinopril tablets by either the previously employed wet-granulated method or by a dry, direct-compression method, of the same type, familiar to those skilled in the art, that is used for other products. The amount of large particle DCPD can be as low as 30% (w/w) of the tablet to obtain the benefit of the invention.

Thus, according to a first aspect of the invention there is provided a solid pharmaceutical composition comprising lisinopril, and an excipient, which comprises DCPD with a specific surface area of less than 1.5 $m^2g^{-1}$ prior to compaction or tabletting in an amount that is at least 30% (w/w) of the composition.

According to a further aspect of the invention there is provided a tablet, produced by either wet granulation tabletting or dry direct-compression tabletting comprising lisinopril, and an excipient, comprising lisinopril and an excipient which comprises DCPD with a specific surface area of less than 1.5 $m^2g^{-1}$ prior to tabletting in an amount that is at least 30% (w/w) of the composition.

According to a further aspect there is provided a tablet comprising lisinopril, an excipient comprising mannitol and DCPD, magnesium stearate, and maize starch.

According to a further aspect of the invention there is provided a pharmaceutical composition in tablet form containing an amount of lisinopril selected from 2.5 mg, 5 mg, 10 mg, 20 mg, 30 mg and 40 mg wherein the amount of lisinopril is expressed as the weight of anhydrous lisinopril (e.g. 30 mg Zestril tablets contain 32.67 mg of lisinopril dihydrate).

In a preferred embodiment of each of the aspects of the present invention, the dibasic calcium phosphate dihydrate has a specific surface area of less than 1.5 $m^2g^{-1}$, more preferably less than 1.25 $m^2g^{-1}$, still more preferably less than 0.9 $m^2g^{-1}$, even still more preferably less than 0.5 $m^2g^{-1}$. In each instance the indicated specific surface area refers the specific surface area prior to any compaction or compression that is performed during tabletting. In one embodiment the dibasic calcium phosphate dihydrate used in the invention has a specific surface area within the range of 0.2 and 1.5 $m^2g^{-1}$, preferably between 0.3 $m^2g^{-1}$ and 0.9 $m^2g^{-1}$.

In a further embodiments of the invention the amount of DCPD is at least 50% (w/w) of the tablet, at least 60% (w/w) of the tablet and in the range of from 50% (w/w) to 70% (w/w) of the tablet. The excipient can further comprise at least 10% (w/w) mannitol. The detailed compositions of specific formulations that are suitable for the present invention can be found in Bavitz, J. F., and Shiromani, P. K., 1986, Drug Dev. Ind. Pharm. 12, 2481–92 and in Shiromani, P. K., and Bavitz, J. F., 1988, Drug Dev. Ind. Pharm. 14, 1375–87.

The reduced amount of lisinopril degradation product is believed to be due to the reduced specific surface area of the DCPD diluent. Accordingly, it will be appreciated that the invention is not restricted to the situation wherein substantially all of the DCPD is within a narrow (but large) size range, but also covers large and small particle size mixtures of DCPD that possess the desired specific surface area. Such mixtures could, for example be formed by combining milled and unmilled DCPD. The SSA limitation is a measure of the total surface area which can therefore accommodate mixtures.

In one particular embodiment the lisinopril used according to the invention is lisinopril dihydrate. However, other solid forms of lisinopril, such as other polymorphs, solvates or monohydrates are also contemplated. Thus, by the term 'any form' we include, solvated and desolvated forms, crystalline forms and amorphous forms.

The present invention relies on the use of grades of DCPD that are commonly used in direct compression techniques thus, individuals or companies interested in preparing lisinopril tablets which routinely practice direct compression/compaction or dry granulation techniques, will particularly benefit from the present invention.

The inventors have discovered that the 2.5 mg dosage tablets of lisinopril are susceptible to less DKP formation over time when DCPD with a lower specific surface area (SSA) than that conventionally used for wet granulation is used. It will be appreciated therefore, that because of the reduced propensity of the DCPD to dehydrate, there will be potential improvements in shelf-life of lisinopril tablets made with DCPD with a specific surface area less than 1.5 $m^2g^{-1}$, particularly of low dosage tablets such as 5 mg or 2.5 mg.

According to a further aspect of the invention there is provided enhanced stability of 2.5 mg tablets of lisinopril comprising using or incorporating dibasic calcium phosphate dihydrate with a specific surface area of less than 1.5 $m^2g^{-1}$. This can be effected by substituting unmilled DCPD for the conventionally used, milled DCPD.

The term stable as used herein, refers to the tendency to remain substantially in the same physical form for at least 6 months, more preferably at least a year, still more preferably at least 3 years, even still more preferably at least 5 years, when stored under ambient conditions (25° C./60%RH) without external treatment.

The invention relies on the use of dibasic calcium phosphate with a specific surface area of less than 1.5 $m^2g^{-1}$. Some manufacturers of dibasic calcium phosphate will be able to provide the desired SSA of the product on demand. Others sell specific grades of dibasic calcium phosphate (i.e. Rhodia Di-Tab™ direct compression grade calcium phosphate dihydrate has a SSA of 0.77 $m^2g^{-1}$; Landin et al., Int. J. Pharm. (1994) 107:247–249). The SSA of dibasic calcium phosphate dihydrate can be determined by the BET method using nitrogen adsorption in a Micromeritics Flowsorb II (Bunauer et al., (1938) J. Am. Chem. Soc., 60:309–319).

'Zestril' and 'Zestoretic' have received regulatory approval for use in the following indications:

Hypertension

'Zestril' is indicated in the treatment of essential hypertension and in renovascular hypertension. It may be used alone or concomitantly with other classes of antihypertensive agents.

'Zestoretic' is indicated in the treatment of hypertension.

Congestive Heart Failure

'Zestril' is indicated in the management of congestive heart failure as an adjunctive treatment with diuretics and, where appropriate, digitalis. High doses reduce the risk of the combined outcomes of mortality and hospitalization.

Acute Myocardial Infarction

'Zestril' is indicated for the treatment of haemodynamically stable patients within 24 hours of an acute myocardial infarction, to prevent the subsequent development of left ventricular dysfunction or heart failure and to improve survival. Patients should receive, as appropriate, the standard recommended treatments such as thrombolytics, aspirin and beta-blockers.

Renal And Retinal Complications of Diabetes Mellitus

In normotensive insulin-dependent and hypertensive non-insulin-dependent diabetes mellitus patients who have incipient nephropathy characterised by microalbuminuria, 'Zestril' reduces urinary albumin excretion rate. 'Zestril' reduces the risk of progression of retinopathy in normotensive insulin-dependent diabetes mellitus patients.

According to the invention there is further provided a pharmaceutical composition comprising lisinopril, as active ingredient, in association with a pharmaceutically acceptable carrier, diluent or excipient and optionally other therapeutic ingredients, produced by a process comprising admixing lisinopril and DCPD with a specific surface area of less than 1.5 $m^2g^{-1}$.

Compositions comprising other therapeutic ingredients are especially of interest in the treatment of hypertension, congestive heart failure, acute myocardial infarction and in renal and retinal complications of diabetes mellitus.

The invention also provides the use of lisinopril and dibasic calcium phosphate dihydrate with a specific surface area less than 1.5 $m^2g^{-1}$ in the manufacture of a medicament for use in the treatment of a cardiovascular related condition, and in particular, a method of treating a hypertensive or congestive heart failure condition which method comprises administering to a subject suffering from said condition a therapeutically effective amount of a lisinopril composition produced by a process comprising admixing lisinopril and DCPD with a specific surface area of less than 1.5 $m^2g^{-1}$.

The invention also provides a pharmaceutical composition comprising lisinopril produced by a process comprising admixing lisinopril and DCPD with a specific surface area of less than 1.5 $m^2g^{-1}$, for use in treating hypertension, congestive heart failure, acute myocardial infarction and in renal and retinal complications of diabetes mellitus.

The invention also provides the use of a lisinopril composition produced by a process comprising admixing lisinopril and DCPD with a specific surface area of less than 1.5 $m^2g^{-1}$ in treating hypertension, congestive heart failure, acute myocardial infarction and in renal and retinal complications of diabetes mellitus.

Any suitable route of administration may be employed for providing the patient with an effective dosage of drug comprising lisinopril according to the invention. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of lisinopril. In all dosage forms lisinopril can be mixed with other suitable constituents. One route of administration is peroral using fast melt tablets.

The compositions of the invention comprise the compound of the invention. The compositions may be conveniently presented in unit dosage forms, and prepared by any methods known in the art of pharmacy.

In the practice of the invention, the most suitable route of administration as well as the magnitude of a therapeutic dose of a pharmaceutical composition comprising lisinopril according to the present invention, in any given case will depend on the nature and severity of the disease to be treated. The dose, and dose frequency, may also vary according to the age, body weight, and response of the individual patient.

In general, a suitable oral dosage form may cover a dose range from 0.5 mg to 150 mg total daily dose, administered in one single dose or equally divided doses. A preferred dosage range is from 1 mg to 60 mg.

Combination therapies comprising lisinopril according to the present invention and other active ingredients in separate dosage forms, or in one fixed dosage form, may also be used. Examples of such active ingredients include anti-bacterial compounds, non-steroidal anti-inflammatory agents, antacid agents, alginates, prokinetic agents, other antihypertensive agents, diuretics, digitalis, thrombolytics, aspirin and beta-blockers.

The invention is further illustrated, but in no way limited, by the following examples.

EXAMPLES

Example 1

Stability time course study of amount of DKP formation in 2.5 mg lisinopril tablets containing different sources of DCPD.

Lisinopril tablets (2.5 mg) were prepared with various types of DCPD according to standard wet granulation methods.

Stability data from Zestril tablets containing 2.5 mg lisinopril dihydrate (Table 1) stored at 50° C. and different particle sizes of DCPD showed that degradation occurred rapidly in those tablets containing milled DCPD (low particle size, high SSA). It is interesting to note that larger particle sizes of DCPD confer stability to the formulation. Potentially giving an advantage of extended stability and thus longer shelf life to the product.

Degradation was determined using analytical high performance liquid chromatography (HPLC).

TABLE 1

Formation of diketopiperazine (DKP) in Zestril 2.5 mg formulation at 50° C. with different specific surface areas (SSA) of Dibasic Calcium Phosphate Dihydrate (DCPD)

| Source of DCPD | SSA ($m^2g^{-1}$) | DKP (%) 1 month | DKP (%) 2 month |
| --- | --- | --- | --- |
| Unmilled Calipharm | 0.40 | 0.50 | 0.97 |
| Kyowa | 0.85 | 0.54 | 1.57 |
| Milled Calipharm | 1.79 | 1.16 | 2.00 |

The enhanced stability, correlating with an increase in particle size, is due to particle shape of the primary particles, and is as a result of the crystal structure of DCPD. The crystal structure of DCPD consists of compact sheets composed of parallel chains in which calcium ions are coordinated by six oxygen atoms of the anions and by two oxygen atoms of the dihydrate waters (Curry and Jones. (1971) J. Chem. Soc A. 23:3725–3729). Two sheets form layers with water interacting between the sheets, this layer like structure is reflected in the plate like morphology of the crystals. Dehydration takes place through the edges of the plate and therefore milling the larger plates increases the surface area available for loss of water resulting in faster dehydration as particle size is reduced.

The stability of DCPD can be assessed by thermogravia-metric analysis (TGA). The determination of the onset for dehydration of DCPD can be used as an indicator of the chemical stability of lisinopril in the formulation. The higher the temperature of dehydration of the first loss of water of DCPD then the more stable is the formulated product. Data for a number of sources of DCPD is shown in Table 2.

TABLE 2

The effect of source of dibasic calcium phosphate dihydrate and the relationship between specific surface area (SSA) and the onset of the first water loss as measured by TGA.

| Source of DCPD | SSA ($m^2g^{-1}$) | Onset for first water loss (° C.) |
| --- | --- | --- |
| Emcompress | 0.36 | 74.7 |
| Calipharm (unmilled) | 0.40 | 72.1 |
| Calipharm (milled) | 1.79 | 56.6 |
| Monsanto | 1.87 | 65.5 |
| Stauffer | 2.10 | 59.2 |

From the data in Table 2 it can be seen that sources of DCPD with specific surface areas less than 1.5 $m^2g^{-1}$ have much higher onsets for the first loss of water of hydration. This reflects the same trend found for the stability of Zestril 2.5 mg formulations (Table 1), in that, formulations containing DCPD having specific surface areas less than 1.5 $m^2g^{-1}$ confer chemical stability to the formulation.

Nitrogen Specific Surface Area

The specific surface area of DCPD is determined by the BET method using nitrogen adsorption in a Micromeritics Flowsorb II. Samples were first degassed under a vacuum at 50° C. for 24 hours.

Thermogravimetric Analysis

Thermogravimetric analysis (TGA, Mettler TG50) was carried out on samples (10–30 mg) over a temperature range of 25–300 ° C. and heating at 10 ° C. $min^{-1}$ using a nitrogen purge (100 ml $min^{-1}$)

Example 2

Formulations

Typical tablet formulations consist of:
a drug (ranging from 1% -50%);
a filler (excipient, diluent), which typically can be dibasic calcium phosphate dihydrate or microcrystalline cellulose or lactose or mannitol;
a binder, which typically can be polyvinylpyrrolidone (PVP) or hydroxy propyl methyl cellulose (HMPC) or microcrystalline cellulose or pre-gelled starch;
a disintegrant, which typically can be crosscarmellose sodium or sodium starch glycolate or starch; and,
a lubricant, which typically can be magnesium stearate and/or a glidant which is typically talc.

Formulations covering the extremes of 1% drug and 50% drug as an example are shown in Table 3.

TABLE 3

Typical tablet formulations containing 1 and 50% drug

| Ingredients | % (w/w) | % (w/w) |
|---|---|---|
| Drug | 1 | 50 |
| Filler | 88 | 29 |
| Binder | 5 | 10 |
| Disintegrant | 5 | 10 |
| Lubricant | 1 | 1 |

In a preferred embodiment of the present invention a typical formulations containing lisinopril or lisinopril and hydrochlorothiazide as the drug (in amounts ranging from 0.5 mg-50 mg) consists of large particle size dibasic calcium phosphate dihydrate as the major excipient, which can be 30%, 40%, 50%, 60%, 70%, 80%, 90%, 95% of the total tablet weight or any amount within the range of 30–95% of the total tablet weight.

The invention is particularly appropriate to lisinopril compositions (such as tablets) that comprise an amount of DCPD that is at least 30%, and preferably at least 50%, of the total composition (i.e. tablet) weight. Tablets that comprise DCPD as the main diluent in an amount of at least 50% of the total tablet weight are particularly preferred.

The detailed compositions of specific formulations that are suitable for the present invention can be found in Bavitz, J. F., and Shiromani, P. K., 1986, Drug Dev. Ind. Pharm. 12, 2481–92 and in Shiromani, P. K., and Bavitz, J. F., 1988, Drug Dev. Ind. Pharm. 14, 1375–87.

What is claimed is:

1. A solid composition comprising between 1% (w/w) and 50% (w/w) lisinopril (1-($N^2$-[(S)-1-carboxy-3-phenylpropyl]-L-lysyl)-L-proline) or lisinopril dihydrate in combination with an excipient in an amount sufficient to make a total composition of 100%, which excipient comprises dibasic calcium phosphate dihydrate (DCPD) in an amount that is at least 30% (w/w) of the total composition, said DCPD having a specific surface area prior to any tabletting of the composition of less than 0.9 $m^2g^{-1}$, and one or more additional ingredients that are fillers, binders, disintegrants, or lubricants or glidants.

2. The solid composition of claim 1, which is a tablet produced by a wet granulation tabletting process.

3. The tablet of claim 2, wherein the excipient comprises DCPD in an amount that is at least 50% (w/w) of the tablet.

4. The tablet of claim 2, wherein the excipient comprises DCPD in an amount that is at least 50% (w/w) of the tablet and the excipient additionally comprises mannitol in an amount that is at least 10% (w/w) of the tablet.

5. The tablet of claim 2, wherein the excipient comprises DCPD in an amount that is at least 50% (w/w) of the tablet.

6. The tablet of claim 2, wherein the excipient comprises DCPD in an amount that is at least 50% (w/w) of the tablet and the excipient additionally comprises mannitol in an amount that is at least 10% (w/w) of the tablet.

7. The solid composition of claim 1, which is a tablet produced by a direct compression tabletting process.

8. The tablet of claim 7, wherein the excipient comprises DCPD in an amount that is at least 50% (w/w) of the tablet.

9. The tablet of claim 7, wherein the excipient comprises DCPD in an amount that is at least 50% (w/w) of the tablet and the excipient additionally comprises mannitol in an amount that is at least 10% (w/w) of the tablet.

10. The tablet of claim 7, wherein the excipient comprises DCPD in an amount that is at least 50% (w/w) of the tablet.

11. The tablet of claim 7, Wherein the excipient comprises DCPD in an amount that is at least 50% (w/w) of the tablet and the excipient additionally comprises mannitol in an amount that is at least 10% (w/w) of the tablet.

12. The tablet of any one of claims 3, 5, 8 or 10, which comprises between 1% (w/w) and 50% (w/w) lisinopril dihydrate.

* * * * *

UNITED STATES PATENT AND TRADEMARK OFFICE
CERTIFICATE OF CORRECTION

PATENT NO.    : 6,462,022 B1
DATED         : October 8, 2002
INVENTOR(S)   : Ronald John Roberts and David Brandon Bowen It is certified that error appears in the above-identified patent and that said Letters Patent is hereby corrected as shown below:

<u>Column 8,</u>
Lines 30 and 32, replace "2" with -- 3 --.
Lines 44 and 46, replace "7" with -- 8 --.
Line 50, replace "3, 5, 8 or 10" with -- 4, 6, 10 or 12 --.

Signed and Sealed this

Twenty-second Day of April, 2003

JAMES E. ROGAN
*Director of the United States Patent and Trademark Office*